United States Patent
Schiff et al.

(10) Patent No.: US 11,464,902 B1
(45) Date of Patent: Oct. 11, 2022

(54) WEARABLE MEDICAMENT DELIVERY DEVICE WITH COMPRESSIBLE RESERVOIR AND METHOD OF USE THEREOF

(71) Applicant: Fresenius Kabi Deutschland GmbH, Bad Homburg (DE)

(72) Inventors: David R. Schiff, Highland Park, NJ (US); Sharon D. West, Elkins Park, PA (US); Jason Zerweck, Media, PA (US)

(73) Assignee: Fresenius Kabi Deutschland GmbH, Bad Homburg (DE)

(*) Notice: Subject to any disclaimer, the term of this patent is extended or adjusted under 35 U.S.C. 154(b) by 0 days.

(21) Appl. No.: 17/178,795

(22) Filed: Feb. 18, 2021

(51) Int. Cl.
*A61M 5/142* (2006.01)
*A61M 5/168* (2006.01)
*A61M 5/148* (2006.01)
*A61M 5/145* (2006.01)
*A61M 5/152* (2006.01)

(52) U.S. Cl.
CPC ........ *A61M 5/14248* (2013.01); *A61M 5/148* (2013.01); *A61M 5/1454* (2013.01); *A61M 5/16881* (2013.01); *A61M 5/152* (2013.01); *A61M 2005/14204* (2013.01); *A61M 2005/14506* (2013.01); *A61M 2205/8281* (2013.01)

(58) Field of Classification Search
CPC .. A61M 5/14248; A61M 5/148; A61M 5/152; A61M 5/1454; A61M 2005/14506; A61M 2205/8281
See application file for complete search history.

(56) References Cited

U.S. PATENT DOCUMENTS

| 4,504,267 A | * | 3/1985 | Parmelee | A61M 5/148 604/174 |
| 5,328,477 A | * | 7/1994 | Sitko | A61M 5/148 222/103 |
| 5,346,476 A | * | 9/1994 | Elson | A61M 5/148 604/246 |
| 5,620,312 A | | 4/1997 | Hyman et al. | |
| 5,897,530 A | * | 4/1999 | Jackson | A61M 5/152 604/132 |

(Continued)

FOREIGN PATENT DOCUMENTS

| EP | 2796157 B1 | 9/2016 |
| WO | WO-2014143770 A1 | 9/2014 |

(Continued)

OTHER PUBLICATIONS

U.S. Appl. No. 17/178,782, filed Feb. 18, 2021, Modular Wearable Medicament Delivery Device and Method of Use Thereof, West, et al.

(Continued)

*Primary Examiner* — Jenna Zhang
(74) *Attorney, Agent, or Firm* — Goodwin Procter LLP

(57) ABSTRACT

A wearable drug delivery device and related methods are described. The wearable drug delivery device can include: a housing; a flexible bag disposed within the housing; a cannula in fluid communication with the flexible bag; and a pumping mechanism for forcing a drug from the flexible bag and into the cannula, wherein the pumping mechanism is proximate the flexible bag and includes a spring-loaded paddle or a driving bag.

10 Claims, 7 Drawing Sheets

(56) References Cited

U.S. PATENT DOCUMENTS

| | | | |
|---|---|---|---|
| 6,213,981 B1* | 4/2001 | Hiejima | A61M 5/1424 604/185 |
| 6,589,229 B1* | 7/2003 | Connelly | A61M 5/14248 604/890.1 |
| 7,147,615 B2 | 12/2006 | Wariar et al. | |
| 8,088,096 B2 | 1/2012 | Lauchard et al. | |
| 8,113,244 B2* | 2/2012 | Kamen | A61M 5/1413 604/404 |
| 9,061,097 B2 | 6/2015 | Holt et al. | |
| 10,569,014 B2 | 2/2020 | Hanson et al. | |
| 10,583,245 B2 | 3/2020 | McCullough et al. | |
| 10,625,018 B2 | 4/2020 | Destefano et al. | |
| 10,646,664 B2 | 5/2020 | Lee et al. | |
| 10,682,474 B2 | 6/2020 | Ring et al. | |
| 10,758,683 B2 | 9/2020 | Gibson et al. | |
| 2002/0072733 A1* | 6/2002 | Flaherty | G16H 20/17 604/890.1 |
| 2002/0123735 A1* | 9/2002 | Rake | A61M 5/148 604/407 |
| 2002/0123740 A1 | 9/2002 | Flaherty et al. | |
| 2002/0123741 A1* | 9/2002 | Rake | A61M 5/148 222/105 |
| 2003/0009131 A1 | 1/2003 | Van Antwerp et al. | |
| 2003/0187395 A1* | 10/2003 | Gabel | A61M 5/14248 604/134 |
| 2006/0287633 A1* | 12/2006 | Yo | A61M 5/145 604/317 |
| 2007/0219597 A1* | 9/2007 | Kamen | A61M 5/16804 128/903 |
| 2011/0105872 A1 | 5/2011 | Chickering, III et al. | |
| 2012/0010594 A1 | 1/2012 | Holt et al. | |
| 2012/0310175 A1* | 12/2012 | Vedrine | A61M 5/1452 604/218 |
| 2013/0006195 A1* | 1/2013 | Sonderegger | A61M 5/14244 604/228 |
| 2014/0100522 A1 | 4/2014 | Nie et al. | |
| 2015/0374919 A1 | 12/2015 | Gibson | |
| 2016/0038689 A1 | 2/2016 | Lee et al. | |
| 2016/0199574 A1 | 7/2016 | Ring et al. | |
| 2016/0296704 A1 | 10/2016 | Gibson | |
| 2016/0354555 A1 | 12/2016 | Gibson et al. | |
| 2017/0147787 A1 | 5/2017 | Albrecht et al. | |
| 2017/0182253 A1 | 6/2017 | Folk et al. | |
| 2017/0361015 A1 | 12/2017 | McCullough | |
| 2017/0368260 A1 | 12/2017 | McCullough et al. | |
| 2018/0001021 A1 | 1/2018 | Wu et al. | |
| 2018/0021508 A1 | 1/2018 | Destefano et al. | |
| 2018/0028747 A1 | 2/2018 | Hanson et al. | |
| 2018/0036476 A1 | 2/2018 | McCullough et al. | |
| 2018/0085517 A1 | 3/2018 | Laurence et al. | |
| 2018/0133447 A1* | 5/2018 | McAllister | A61M 37/0015 |
| 2018/0256823 A1 | 9/2018 | Nazzaro et al. | |
| 2018/0304014 A1 | 10/2018 | Knudsen et al. | |
| 2019/0022306 A1 | 1/2019 | Gibson et al. | |
| 2019/0050375 A1 | 2/2019 | Fitzgibbon et al. | |
| 2019/0060562 A1 | 2/2019 | Olivas et al. | |
| 2019/0083702 A1 | 3/2019 | Nekouzadeh et al. | |
| 2019/0134296 A1 | 5/2019 | Barbedette et al. | |
| 2019/0143043 A1 | 5/2019 | Coles et al. | |
| 2019/0143047 A1 | 5/2019 | Jazayeri et al. | |
| 2019/0151544 A1 | 5/2019 | Stonecipher | |
| 2019/0167908 A1 | 6/2019 | Fitzgibbon et al. | |
| 2019/0192766 A1 | 6/2019 | Stonecipher | |
| 2019/0247579 A1 | 8/2019 | Damestani et al. | |
| 2019/0275235 A1 | 9/2019 | Barmaimon et al. | |
| 2019/0275241 A1 | 9/2019 | Ring et al. | |
| 2019/0307958 A1 | 10/2019 | Yang | |
| 2019/0328965 A1 | 10/2019 | Moberg | |
| 2019/0365986 A1 | 12/2019 | Coiner et al. | |
| 2019/0381238 A1 | 12/2019 | Stonecipher et al. | |
| 2020/0069875 A1 | 3/2020 | Nazzaro et al. | |
| 2020/0179609 A1 | 6/2020 | Tan-Malecki et al. | |
| 2020/0188585 A1 | 6/2020 | Petisce et al. | |
| 2020/0253525 A1 | 8/2020 | Zhang et al. | |
| 2021/0069411 A1 | 3/2021 | Demers et al. | |

FOREIGN PATENT DOCUMENTS

| | | | |
|---|---|---|---|
| WO | WO-2015187797 A1 | 12/2015 | |
| WO | WO-2016100055 A1 | 6/2016 | |
| WO | WO-2016130679 A2 | 8/2016 | |
| WO | WO-2016133947 A1 | 8/2016 | |
| WO | WO-2016145094 A2 | 9/2016 | |
| WO | WO-2016130679 A3 | 11/2016 | |
| WO | WO-2017120178 A1 | 7/2017 | |
| WO | WO-2017200989 A1 | 11/2017 | |
| WO | WO-2018081234 A1 | 5/2018 | |
| WO | WO-2018151890 A1 | 8/2018 | |
| WO | WO-2018164829 A1 | 9/2018 | |
| WO | WO-2018165499 A1 | 9/2018 | |
| WO | WO-2018183039 A1 | 10/2018 | |
| WO | WO-2018226515 A1 | 12/2018 | |
| WO | WO-2018226565 A1 | 12/2018 | |
| WO | WO-2018236619 A1 | 12/2018 | |
| WO | WO-2018237225 A1 | 12/2018 | |
| WO | WO-2019014014 A1 | 1/2019 | |
| WO | WO-2019018169 A1 | 1/2019 | |
| WO | WO-2019022950 A1 | 1/2019 | |
| WO | WO-2019022951 A1 | 1/2019 | |
| WO | WO-201932101 A1 | 2/2019 | |
| WO | WO-2019032482 A2 | 2/2019 | |
| WO | WO-2019070472 A1 | 4/2019 | |
| WO | WO-2019070552 A1 | 4/2019 | |
| WO | WO-2019074579 A1 | 4/2019 | |
| WO | WO-2019089178 A1 | 5/2019 | |
| WO | WO-2019090303 A1 | 5/2019 | |
| WO | WO-2019143753 A1 | 7/2019 | |
| WO | WO-2020112515 A1 * | 6/2020 | A61K 9/19 |

OTHER PUBLICATIONS

U.S. Appl. No. 17/178,799, filed Feb. 18, 2021, Wearable Medicament Delivery Device With Leakage and Skin Contact Sensing and Method of Use Thereof, Schiff, et al.

* cited by examiner

WEARABLE MEDICAMENT DELIVERY DEVICE WITH COMPRESSIBLE RESERVOIR AND METHOD OF USE THEREOF

TECHNICAL FIELD

The present disclosure generally relates to drug delivery devices and, more particularly, a drug delivery device capable of being worn by a patient while the drug delivery device delivers a drug to the patient.

BACKGROUND

Delivery of medicaments, e.g., liquid drugs, to a patient via injection using a needle or syringe is well-known. More recently, devices that automate the delivery of medicaments have been introduced. These devices (which are commonly referred to as "on-body devices" or "on-body injectors") are mounted or otherwise secured to the body of the patient (e.g., to the arm or abdomen) and remain in place for an extended amount of time (on the order of hours or days), injecting an amount of the medicament into the body of the patient at one or more scheduled times. For example, a device may be configured to deliver a medicament over the span of 45 minutes, with delivery beginning 27 hours after the device has been activated and applied to a patient (to ensure that the medicament is not delivered sooner than 24 hours after a medical procedure or treatment). These devices improve upon manual methods by obviating the need for the patient to inject themselves with the medicament (which carries heightened risks of the patient improperly administering the injection or injecting the medicament at an inappropriate time) or to return to a medical facility for one or more injections by a technician or medical professional.

One known on-body device 10 is shown in FIGS. 1 and 2. The device 10 of FIG. 1 includes a housing 12 that contains or encloses the functional components of the device 10, which are shown in FIGS. 3 and 4.

The internal components of the device 10 include a reservoir 14 that is configured to be filled with a medicament to be delivered to the patient. An upper surface of the housing 12 includes a fill indicator 16 that provides a visual indication of the amount of fluid in the reservoir 14. In addition to the fill indicator 16, the upper surface of the housing 12 may include printed information, such as information regarding the medicament to be delivered. The upper surface of the housing 12 may be formed of a translucent material, which allows light from a status light 18 (which may be configured as a light-emitting diode) mounted within the housing 12 (FIG. 1) to be seen through the upper surface of the housing 12. The status light 18 is electrically coupled to a controller or processor (which may be a CPU or MPU configured as a computer chip mounted to a printed circuit board positioned within the housing 12, for example) that carries software for executing a medicament delivery routine. The status light 18 receives signals from the controller and emits light to provide information regarding a status of the device 10. This may include emitting differently colored light and/or emitting light in different flashing patterns to indicate different conditions, such as a blinking orange light to indicate that the device 10 is ready to be applied to a patient, a blinking green light to indicate proper operation of the device 10, and a blinking red light to indicate an error or other condition. A battery 20 provides power to the status light 18 and the other electrical components of the device 10.

The medicament is injected into the reservoir 14 using a (typically pre-filled) syringe 22 via a port 24 incorporated into the bottom or underside of the housing 12 (FIG. 4) and fluidly connected to the reservoir 14. FIGS. 1 and 2 illustrate an applicator 26 that is removably associated with the underside of the housing 12 and used in combination with the syringe 22 to fill the reservoir 14 via the port 24. The medicament is most typically injected into the reservoir 14 by a medical professional immediately before the device 10 is secured to the patient to ensure that the proper medicament is supplied, along with the proper amount.

A piston or plunger 28 (FIG. 4) positioned within the reservoir 14 is moved (from left to right, in the orientation of FIG. 4) as the space within the reservoir 14 is filled by the inflowing medicament. Movement of the piston 28 into its final position (when the reservoir 14 has been filled with the appropriate amount of the medicament) causes a portion of a rod associated with the piston 28 to extend from the reservoir 14 to create an electrical connection, which activates the device 10. Activation of the device 10 may include a signal, such as a buzzer providing an audible indication that the device 10 has been activated and/or a light emitted by the status light 18.

When the device 10 has been activated, it is mounted or secured to the body of the patient. The applicator 26 is first removed from the underside of the housing 12 and discarded, followed by a pull tab 30 being manipulated to remove a release film from an adhesive pad 32 associated with the underside of the housing 12. The housing 12 is then pressed against the body of the patient, with the adhesive pad 32 facing the body. An adhesive present on the adhesive pad 32 causes the adhesive pad 32 (and, hence, the housing 12) to adhere to the body.

Some predetermined time after the device 10 has been activated (which may be on the order of three to five minutes, for example), a distal end portion of a cannula 34 is introduced into the skin of the patient via a cannula window 36 defined in the housing 12 (FIGS. 3 and 4). The cannula 34 (which remains partially positioned within the skin of the patient for as long as the device 10 is in use) is formed of a flexible or semi-rigid material, such as a plastic material, for improved patient comfort.

As the cannula 34 is not itself configured to pierce the skin, an associated needle 38 is provided within the lumen of the cannula 34, with a sharp or beveled distal end of the needle 38 extending out of a distal end of the cannula 34. A midsection of the needle 38 is mounted within a needle carriage 40, while a proximal end 42 of the cannula 34 is mounted within a cannula carriage 44 that is initially positioned directly adjacent to the needle carriage 40. The needle carriage 40 is pivotally connected to an end of a linkage or crank arm 46, with an opposite end of the linkage 46 being associated with a torsion spring 48. At the designated time (e.g., 3-5 minutes after the device 10 has been activated), the controller causes a lever (not visible) to be released, which allows the spring 48 to recoil, in turn rotating the linkage 46, which rotation causes the needle carriage 40 to move along a linear track 50 from a first position adjacent to the spring 48 (FIG. 3) to a second position spaced away from the spring 48. Movement of the needle carriage 40 causes corresponding movement of the cannula carriage 44 along the track 50, with the cannula 34 and the distal portion of the needle 38 moving together in a direction away from the spring 48. Moving the carriages 40 and 44 into the second position causes the sharp distal end of the needle 38 to advance out of the housing 12 via the cannula window 36 and pierce the skin. The cannula 34 is carried by or moves along with the distal portion of the needle 38, such that the needle 38 piercing the skin will also cause the distal end of the cannula 34 to enter into the skin.

Continued recoiling of the spring 48 causes further rotation of the linkage 46, which has the effect of moving the needle carriage 40 back toward the spring 48 (i.e., back toward its first position). Rather than moving along with the needle carriage 40, the cannula carriage 44 is held in its second position (FIG. 3) by a lock or latch 52. As the movement of the needle carriage 40 is not restricted by the lock or latch 52, the needle carriage 40 will return to its first position, while the cannula carriage 44 remains in its second position (with the final positions of both carriages 40 and 44 shown in FIG. 3).

Movement of the needle carriage 40 in a proximal direction away from the cannula carriage 44 causes the needle 38 to partially (but not fully) retract from the cannula 34. In the final condition shown in FIG. 3, the distal end of the needle 38 is positioned within the cannula 34 (e.g., adjacent to a midsection or midpoint of the cannula 34), while the distal end of the cannula 34 remains positioned within the skin. A proximal end of the needle 38 extends into fluid communication with the reservoir 14, such that the needle 38 provides a fluid path from the reservoir 14 to the cannula 34 when the carriages 40 and 44 are in the final condition illustrated in FIG. 3. Due to the distal end of the cannula 34 remaining positioned within the skin, subsequent advancement of the medicament out of the reservoir 14 (e.g., 27 hours after the device 10 has been activated) will cause the medicament to move into the needle 38 (via the proximal end of the needle 38), through the needle 38 (to its distal end), and into the cannula 34. The medicament is then delivered to the patient (e.g., over the course of a 45-minute session) via the distal end of the cannula 34 positioned within the skin.

As for the mechanism by which the medicament is advanced out of the reservoir 14, the device 10 includes a lever 54 mounted to a pivot point 56 (FIG. 4). The lever 54 includes a first arm 58 configured and oriented to interact with a first gear 60 and a second arm 62 configured and oriented to interact with a second gear 64. A tab 66 extends from an opposite end of the lever 54 and is configured and oriented to alternately move into and out of contact with two electrical contacts 68 and 70 (electrically coupled to a printed circuit board, which is not shown) as the lever 54 pivots about the pivot point 56.

A first wire or filament 72 extends from the lever 54, around a first pulley 74, and into association with a first electrical contact 76. A second wire or filament 78 extends from the lever 54 in the opposite direction of the first wire 72, around a second pulley 80, and into association with a second electrical contact 82. The wires 72 and 78 allow the lever 54 to stay electrically coupled to the electrical contacts 76 and 82 (which are electrically coupled to the above-referenced printed circuit board) as the lever 54 pivots about the pivot point 56.

At the designated time (e.g., 27 hours after the device 10 has been activated), the controller provides commands that cause the lever 54 to be alternately pivoted about the pivot point 56 in opposite first and second directions. Pivotal movement of the lever 54 in the first direction will cause the first arm 58 of the lever 54 to engage and rotate the first gear 60 an incremental amount, while pivotal movement of the lever 54 in the second direction will cause the second arm 62 of the lever 54 to engage and rotate the second gear 64 an incremental amount (in the same direction in which the first gear 60 is rotated by the first arm 58). Both gears 60 and 64 are contained within a single part and are associated with a common shaft 84 (FIG. 3), such that rotation of either gear 60, 64 will cause the shaft 84 to rotate about its central axis. The shaft 84 is mechanically coupled to the piston 28 within the reservoir 14, with rotation of the shaft 84 causing the piston 28 to move toward its initial position (e.g., by a threaded connection whereby rotation of the shaft 84 is translated into movement of the piston 28 along the length of the reservoir 14). As the piston 28 moves toward its initial position (from right to left in the orientation of FIG. 4), it will force the medicament out of the reservoir 14 via the proximal end of the needle 38. As described above, the medicament will flow through the needle 38, into and through the cannula 34, and into the body of the patient.

After the medicament has been delivered (e.g., over the course of a 45-minute session), the controller alerts the patient via a visual cue from the status light 18 and/or an audible cue from the buzzer that medicament delivery is complete. Subsequently, the patient removes the device 10 from their skin and discards the device 10.

While devices of the type described above have proven adequate, there is room for improvement of them. For example, there is a need for on-person or wearable medicament delivery devices that provide more efficient and reliable medicament pumping mechanisms. There is also a need for medicament delivery devices that are smaller in size, lower profile, less likely to be caught on clothing or become dislodged, and/or more comfortable to wear.

SUMMARY

In general, in one aspect, the subject matter of this disclosure relates to a wearable drug delivery device including: a housing; a flexible bag disposed within the housing; a cannula in fluidic communication with the flexible bag; and a pumping mechanism for forcing a drug from the flexible bag and into the cannula, the pumping mechanism proximate the flexible bag and including one of: a spring-loaded paddle; or a driving bag.

In certain examples, the pumping mechanism can include the spring-loaded paddle. The spring-loaded paddle can include a hinged connection. The spring-loaded paddle can be driven by a torsion spring or a compression spring. The pumping mechanism can include the driving bag. The driving bag can include a frangible baffle between a first chamber and a second chamber, wherein the first chamber includes a first reactant, and wherein the second chamber includes a second reactant. The device can include an actuatable trigger for breaking the frangible baffle to achieve contact between the first reactant and the second reactant, which can result in a gas evolution chemical reaction. The housing can include a flexible outer shell and/or a housing height less than 12 mm. The device can include a valve for controlling fluid flow through the cannula.

In another aspect, the subject matter of this disclosure relates to a method of delivering a drug. The method includes: (i) providing a wearable drug delivery device including: a housing; a flexible bag disposed within the housing; a cannula in fluidic communication with the flexible bag; and a pumping mechanism including one of a spring-loaded paddle or a driving bag; and (ii) activating the pumping mechanism to force a drug from the flexible bag and into the cannula.

In some implementations, the pumping mechanism includes the spring-loaded paddle. Activating the pumping mechanism can include pivoting the spring-loaded paddle about a hinged connection. Pivoting the spring-loaded paddle can include driving the spring-loaded paddle with a torsion spring or a compression spring. The pumping mechanism can include the driving bag. The driving bag can include a frangible baffle between a first chamber and a second chamber, wherein the first chamber includes a first reactant, and wherein the second chamber includes a second reactant. The method can include breaking the frangible baffle to achieve contact between the first reactant and the second reactant. The contact can result in a gas evolution chemical reaction. The housing can include a flexible outer shell and/or a housing height less than 12 mm. The method can include controlling fluid flow through the cannula using a valve. The drug or medicament can include pegfilgrastim.

These and other objects, along with advantages and features of embodiments of the present invention herein disclosed, will become more apparent through reference to the following description, the figures, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which.

DETAILED DESCRIPTION

It is contemplated that apparatus, systems, methods, and processes of the claimed invention encompass variations and adaptations developed using information from the embodiments described herein. Adaptation and/or modification of the apparatus, systems, methods, and processes described herein may be performed by those of ordinary skill in the relevant art and are considered to be within the scope of the disclosed invention.

It should be understood that the order of steps or order for performing certain actions is immaterial, so long as the invention remains operable. Moreover, two or more steps or actions may be conducted simultaneously.

Figure 5A:
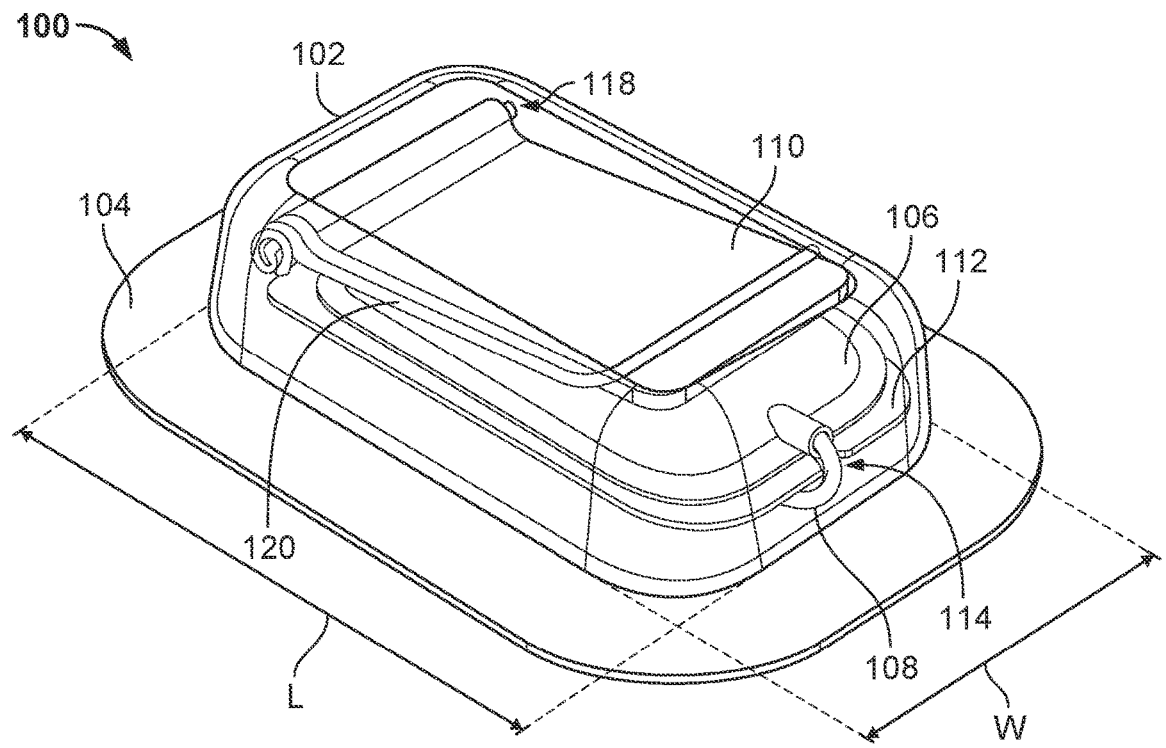
FIG. 5A is a schematic, perspective view of a drug delivery device having a paddle and a torsion spring, in accordance with certain embodiments of the invention.
Figure 5B:
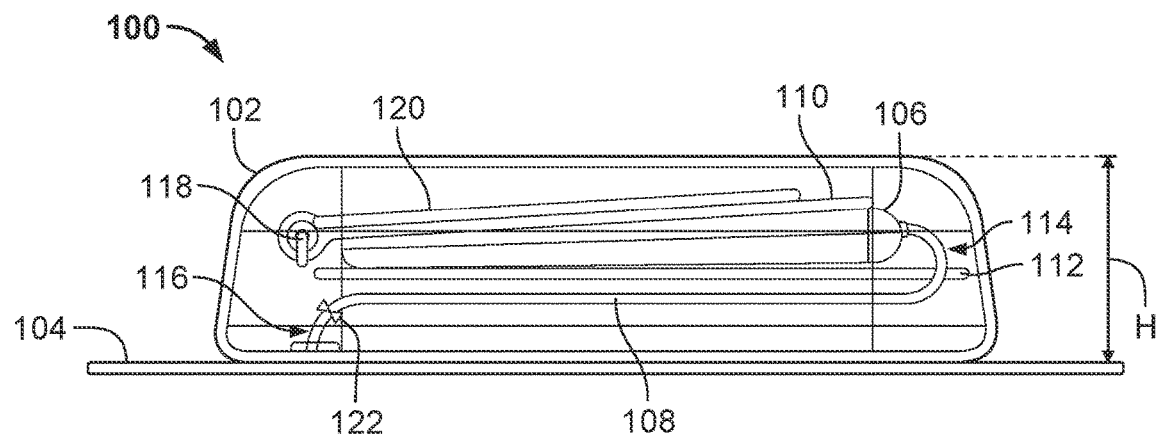
FIG. 5B is a schematic, side view of the drug delivery device of FIG. 5A.

Referring to FIGS. 5A and 5B, in some examples, an on-body or wearable drug delivery device 100 includes a housing 102, an adhesive pad 104, a flexible bag 106 containing a drug (e.g., a liquid drug), a cannula 108 in fluid communication with the flexible bag 106, and a paddle 110 disposed on or proximate to the flexible bag 106. While this disclosure may describe the drug delivery device 100 as delivering a liquid drug, in general and in various embodiments the device 100 can be adapted to deliver any medicament (e.g., drug, biologic, etc.) in any form (e.g., liquid, gel, powder, etc.). In general, the housing 102 is attached to the adhesive pad 104, which can be used to secure the device 100 to a patient. The flexible bag 106 and the paddle 110 can be disposed within the housing 102. The flexible bag 106 can be substantially flat and/or arranged in a plane that is substantially parallel to a plane defined by the adhesive pad. In other embodiments, the flexible bag 106 can be arranged in different orientations. In the depicted example, the flexible bag 106 is disposed between a support 112 and the paddle 110. The support 112 can be or include a flat plate and/or one or more other components disposed within the housing 102. In some examples, the support 112 can be or include a portion of the housing 102 and/or the adhesive pad 104. A proximal end 114 of the cannula 108 can be connected to the flexible bag 106 (e.g., at an end or edge), and a distal end 116 of the cannula 108 exits the housing 102 (e.g., through the adhesive pad 104) for insertion into the patient's skin.

In certain implementations, the paddle 110 can be used to pump the drug from the flexible bag 106, through the cannula 108, and into the patient. The paddle 110 can be attached at one end to a hinge 118, which allows the paddle 110 to rotate or pivot about the hinge 118. A torsion spring 120 may be provided to press the paddle 110 towards and/or into the flexible bag 106. In such embodiments, the pivoting action of the paddle 110 compresses or squeezes the flexible bag 106 between the paddle 110 and the support 112, thereby increasing a pressure inside the flexible bag 106. The increased pressure can pump the drug from the flexible bag 106 and into the cannula 108.

In various implementations, the device 100 includes a valve 122 for regulating fluid flow from the flexible bag 106 and/or through the cannula 108. The valve 122 can be mechanically and/or electrically actuated to open and close, as needed, to deliver desired amounts of drug to the patient. For example, while the paddle 110 may be continuously squeezing the flexible bag 106, the drug may be permitted to flow from the flexible bag 106 only when the valve 122 is open. The device can include a controller or processor and battery power, as needed, to regulate the opening and closing of the valve 122. In some examples, the valve 122 can stop the flow by crimping or squeezing the cannula 108.

Figure 6A:
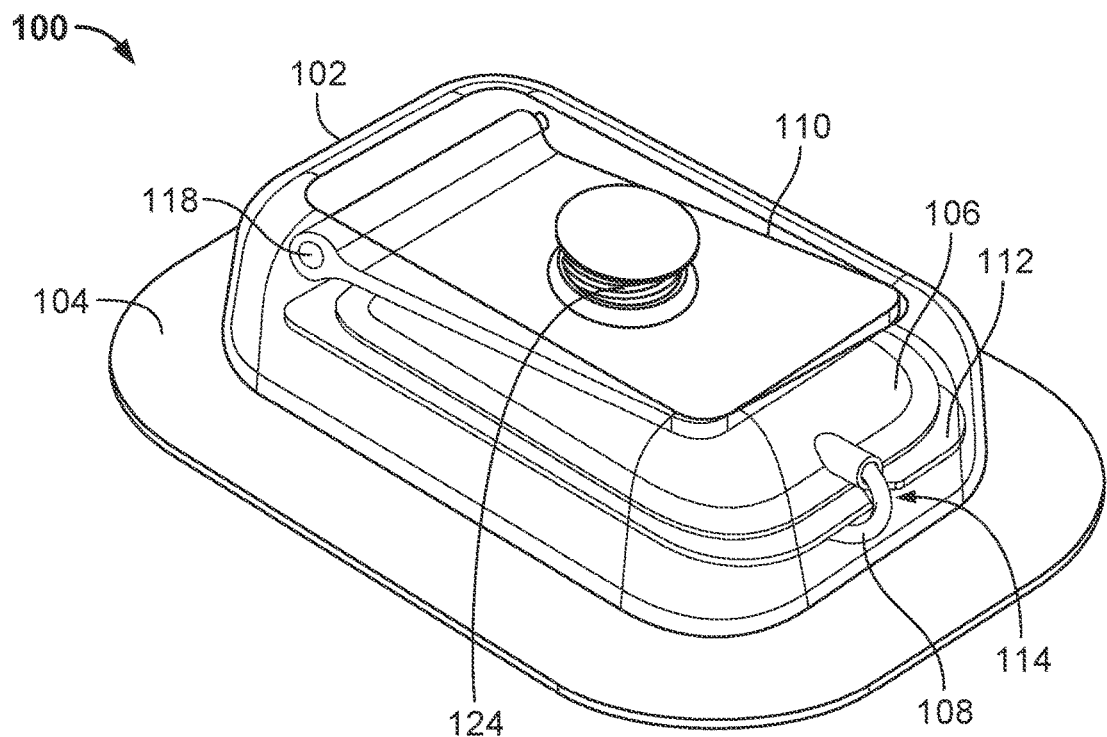
FIG. 6A is a schematic, perspective view of a drug delivery device having a paddle and a compression spring, in accordance with certain embodiments of the invention.
Figure 6B:
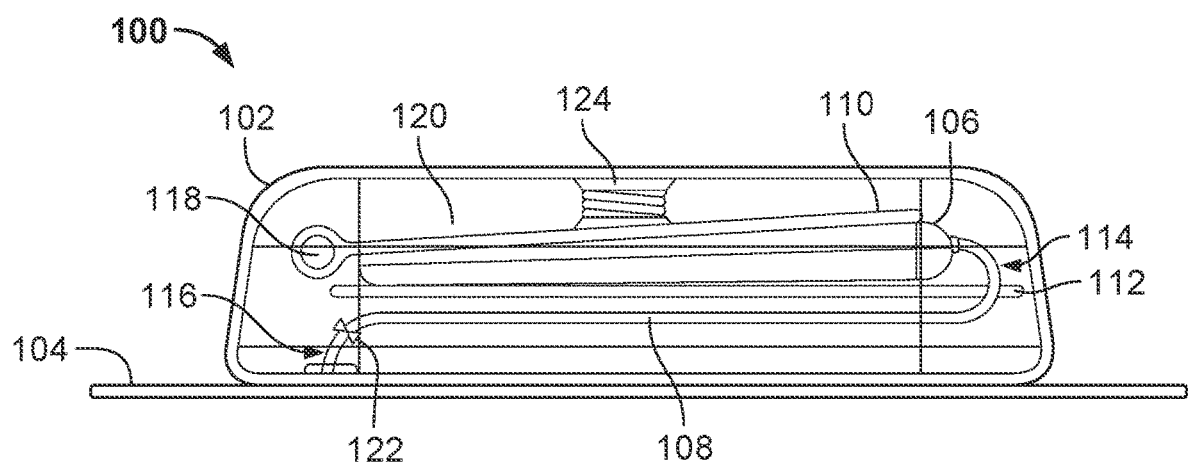
FIG. 6B is a schematic, side view of the drug delivery device of FIG. 6A.

Referring to FIGS. 6A and 6B, in an alternative example, the device 100 utilizes a compression spring 124 (in addition to or instead of the torsion spring 120) to pivot or press the paddle 110 towards and/or into the flexible bag 106. The compression spring 124 can be positioned between the paddle 110 and a top portion of the housing 102, as shown. Other types of springs or forcing mechanisms for pivoting or pressing the paddle 110 are contemplated. For example, the device 100 can utilize or include, an extension spring, a Belleville spring, a drawbar spring, a volute spring, a garter spring, a flat spring, a gas spring, and/or an air spring. Additionally or alternatively, the paddle 110 can be pivoted or forced using one or more pneumatic components, hydraulic components, and/or electrical components (e.g., a motor).

Figure 7A:
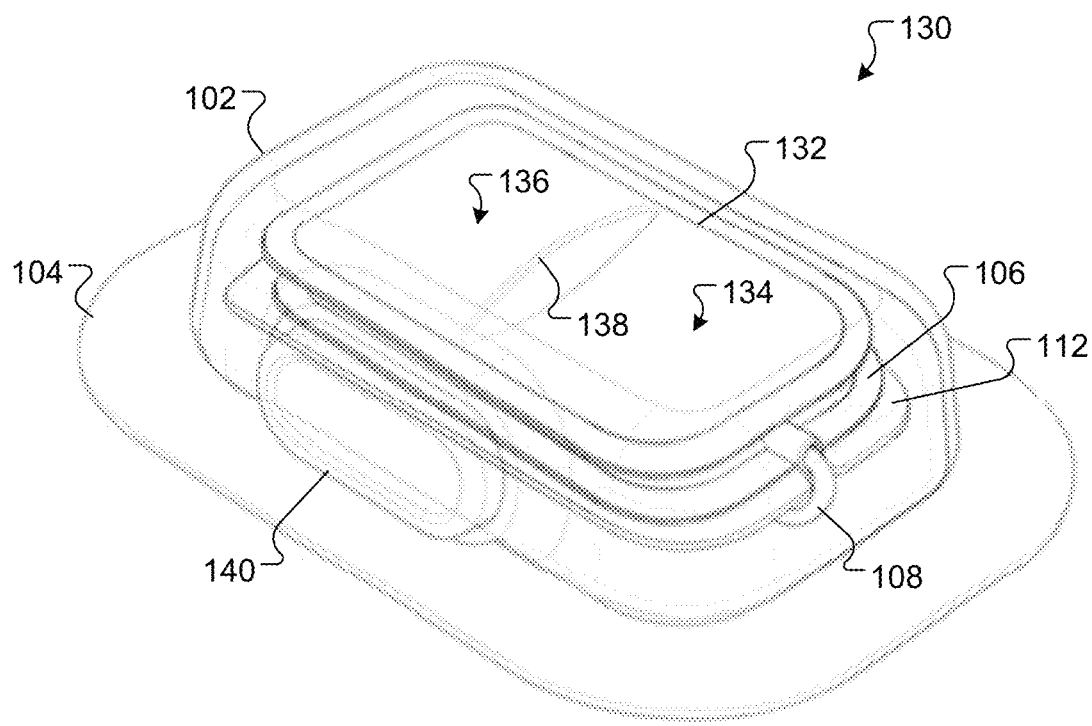
FIG. 7A is a schematic, perspective view of a drug delivery device having a driving bag, in accordance with certain embodiments of the invention.
Figure 7B:
FIG. 7B is a schematic, side view of the drug delivery device of FIG. 7A in which the driving bag is in an unexpanded state.
Figure 7C:
FIG. 7C is a schematic, side view of the drug delivery device of FIG. 7A in which the driving bag is in an expanded or inflated state.
Figure 8:
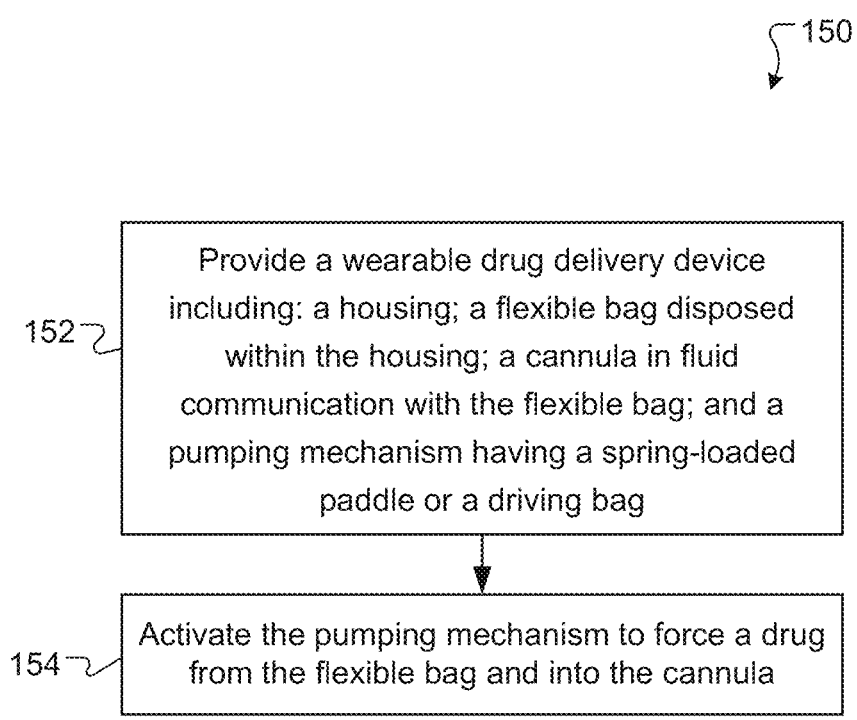
FIG. 8 is a flowchart of a method of delivering a drug, in accordance with certain embodiments of the invention.

Referring to FIGS. 7A, 7B, and 7C, in certain implementations, a wearable drug delivery device 130 includes the housing 102, the adhesive pad 104, the flexible bag 106 containing the drug, the cannula 108 in fluid communication with the flexible bag 106, the valve 122 for regulating fluid flow through the cannula 108, and a driving bag 132 disposed on or proximate to the flexible bag 106. In some embodiments, the driving bag 132 includes a first chamber 134 and a second chamber 136 separated by a frangible baffle 138. The first chamber can include one or more first reactants and the second chamber can include one or more second reactants, and the frangible baffle 138 can serve as a barrier to prevent contact between the one or more first reactants and the one or more second reactants. To pump the drug from the flexible bag 106, a user of the device 130 (e.g., the patient) can press a button 140 on the device 130, which can act as a trigger for breaking the frangible baffle 138. The button 140 can be or include, for example, a mechanically, electrically, and/or remotely actuated trigger that is capable of breaking or rupturing the frangible baffle 130. In one example, the button 140 can compress the driving bag 132 and cause the frangible baffle 130 to rupture and/or detach from an inner surface of the driving bag 138, such that the one or more first reactants and the one or more second reactants can come into contact and/or mix with one another. The frangible baffle 130 can be constructed of or include one or more brittle materials and/or thin portions that are configured to break or rupture when subjected to stress introduced by the button 140. Once the one or more first reactants and the one or more second reactants come into contact, a chemical reaction can take place that causes the driving bag 132 to expand or inflate. For example, the one or more first reactants and the one or more second reactants can react to generate gas and/or produce a foam. As the driving bag 132 expands, the flexible bag 106 can be compressed or squeezed between the driving bag 132 and the support 112, which increases the pressure in the flexible bag 106 and causes the drug to flow from the flexible bag 106 and into the cannula 108. FIG. 7B shows the driving bag 132 in an initial, unexpanded state, with the flexible bag 106 full or nearly full of the drug. FIG. 7C shows the driving bag 132 in a final, expanded state, with the flexible bag 106 empty or nearly empty of the drug. The valve 122 can be opened and closed to regulate flow through the cannula 108, as needed.

In various examples, the one or more first reactants and the one or more second reactants can include any combination of reactants that, when mixed, react with one another to expand in volume or size (e.g., in a one-way chemical reaction). A product of the reaction can be or include, for example, a gas (e.g., in a gas evolution reaction) and/or a foam, such as an expanding foam (e.g., an expanding polyurethane foam). In one example, the one or more first reactants include an isocyanate and/or a polyisocyanate, and the one or more second reactants include a mix of polyol, water, surfactant, and/or catalyst, for producing a polyurethane foam. In another example, the gas evolution reaction can occur between an acid and a carbonate. When choosing the reactants and products for the reaction, an amount of expansion relative to starting volumes should be assessed, along with safety considerations related to use of such materials in a wearable device.

In other embodiments, the driving bag 132 can be expanded to compress the flexible bag 106 using other techniques. For example, the driving bag 132 can be inflated using a pump, an air compressor, a cannister or cartridge of compressed air or other gas, or other known inflation techniques or devices, which can be in fluidic communication with the driving bag 132. The flexible bag 106 and/or the driving bag 132 can be made of a variety of flexible and/or nonpermeable materials, including, for example, polyethylene, polypropylene, polyester, other polymeric materials, aluminum, other metallic materials, or any combination thereof. In one example, the flexible and/or nonpermeable materials include a laminated film in which at least one layer includes aluminum or other impermeable material.

Figure 1:
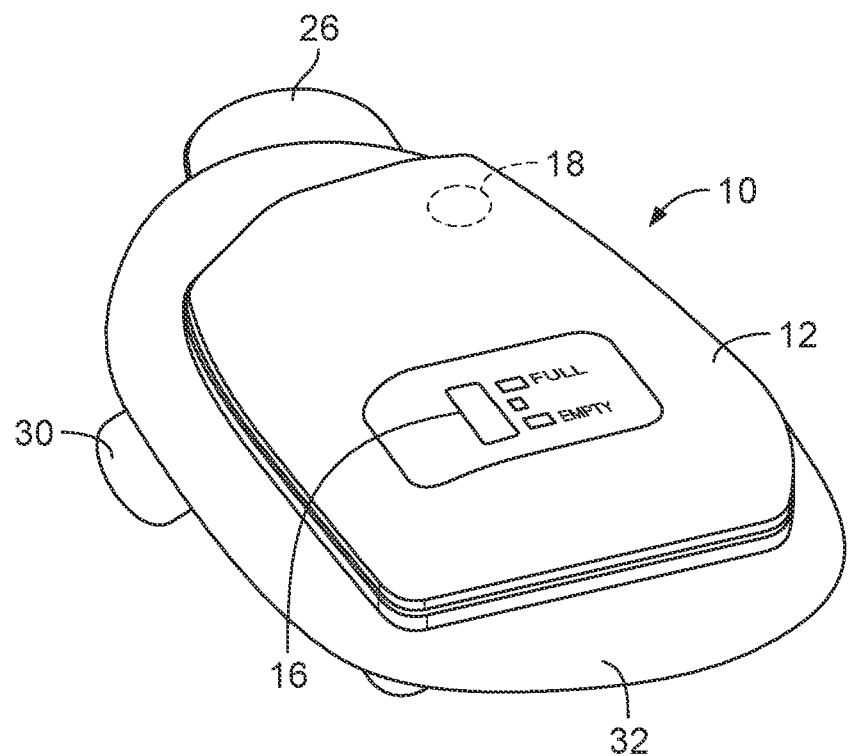
FIG. 1 is a schematic, perspective view of a known drug delivery device.
Figure 2:
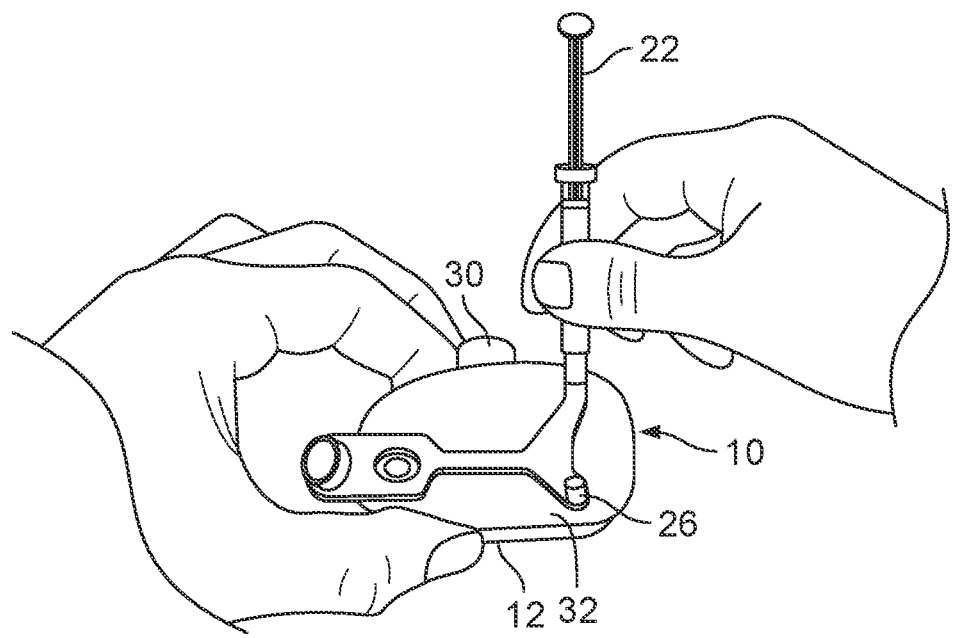
FIG. 2 is a schematic, bottom view of the device of FIG. 1 being filled with a drug.
Figure 3:
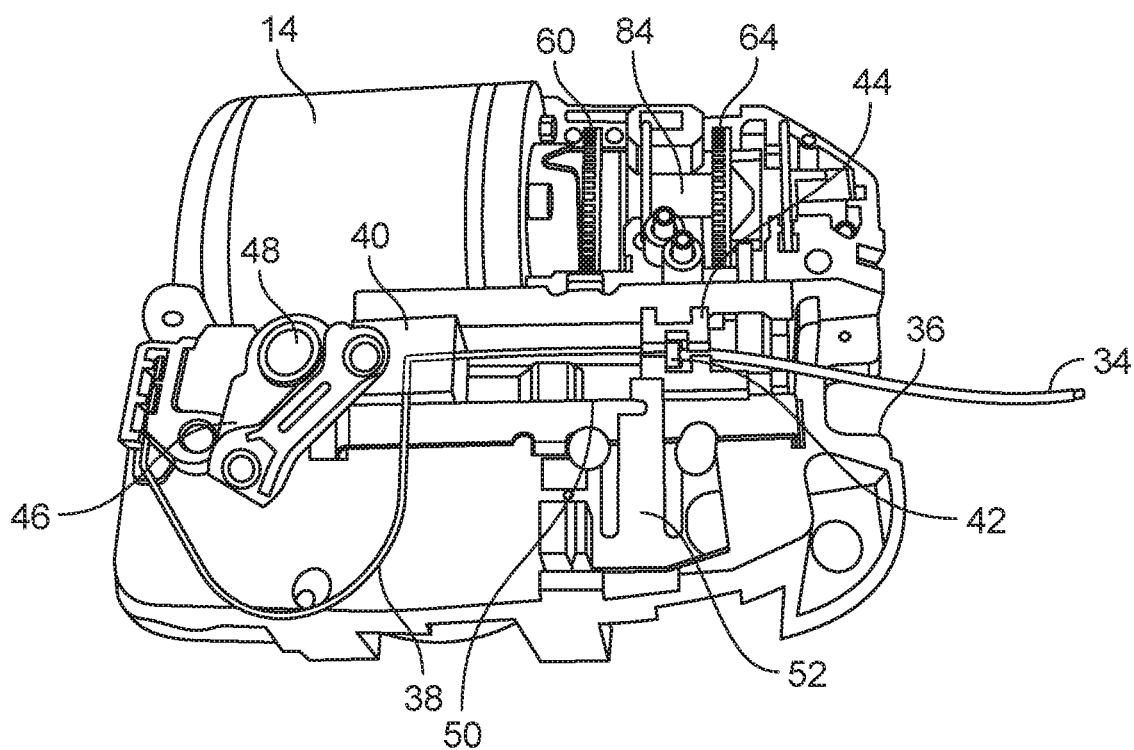
FIGS. 3 and 4 are images of functional components of the device of FIG. 1 in which an exterior housing of the device has been removed.
Figure 4:
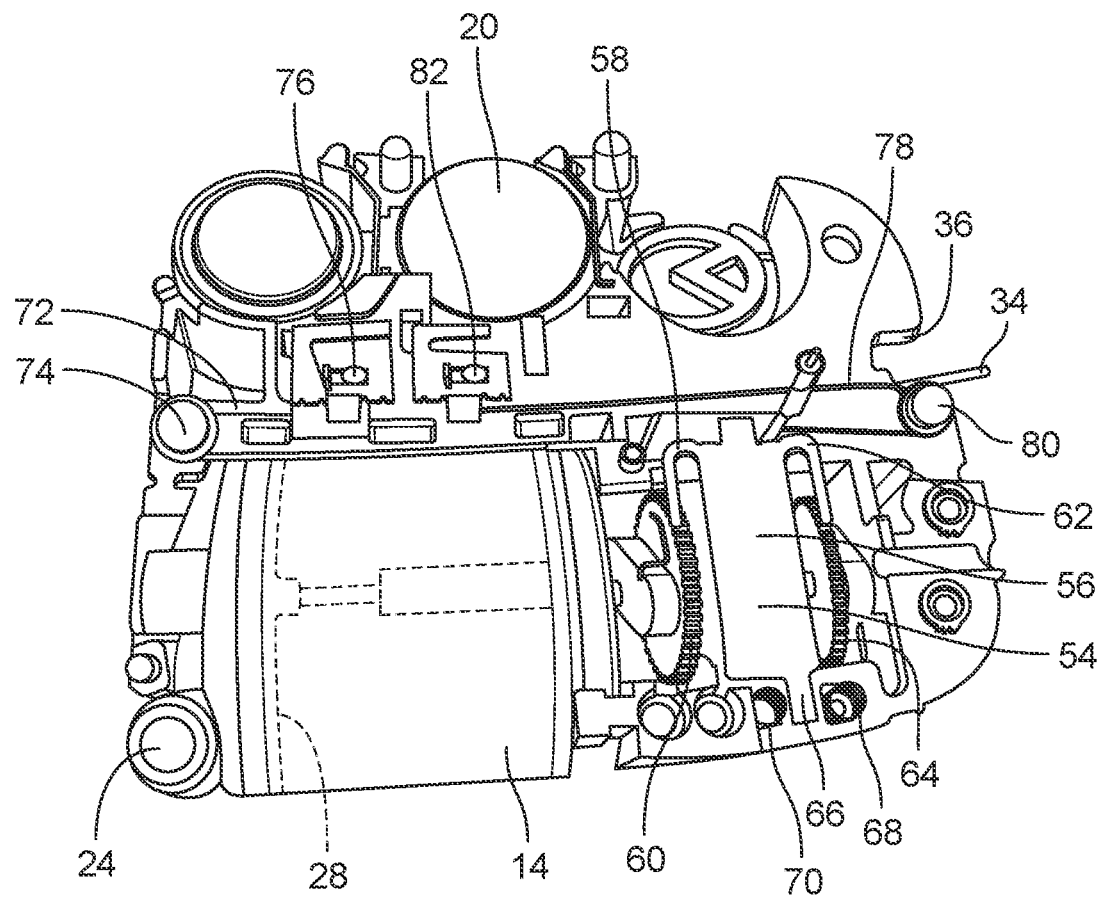

Advantageously, use of the flexible bag 106 and the pumping mechanisms described herein (e.g., including the paddle 110 and the driving bag 132) can allow the housing 102 to be more compact and/or have a lower profile compared to existing or previous designs. Referring again to FIGS. 5A and 5B, the housing 102 can have a length L, a width W, and a height H, any of which can be less than corresponding dimensions for existing or previous designs. For example, the height H of the housing 102 can be 10% less, 25% less, or 50% less than corresponding heights of existing or previous designs, such as the design shown in FIG. 1. The lower profile of the housing 102 can make the devices described herein less likely to be caught on clothing and/or dislodged, which can lead to leakage.

Example low, high, and typical values for the length L, the width W, the height H, and other parameters for the drug delivery devices described herein are provided in Table 1. The listed values can be minimum, maximum, or average dimensions. Various embodiments include any parameter value (e.g., integer or decimal value) within the cited ranges. For example, the length L of the housing 102 can be 25, 26, 27, . . . , 74, or 75 mm. Express support and written description of these values for each parameter are hereby represented.

TABLE 1

Exemplary parameters for medicament delivery device.

| Parameter | Low | Typical | High |
|---|---|---|---|
| Housing Length L (mm) | 25 | 50 | 75 |
| Housing Width W (mm) | 20 | 40 | 60 |
| Housing Height H (mm) | 6 | 12 | 18 |
| Flexible Bag Capacity (cm$^3$) | 0.1 | 1 | 5 |
| Flexible Bag Pumping Pressure (kPa, gauge) | 10 | 100 | 1000 |

Additionally or alternatively, use of flexible components (e.g., the flexible bag 106) can allow the housing 102 to be made of or include soft or flexible materials. For example, the housing 102 can be constructed of thin or flexible plastic materials that allow the housing 102 to be more comfortable to wear and/or capable of bending or deforming, as needed, in response to movement of the patient's body. In some instances, for example, the housing 102 can be made of a flexible polymeric material (e.g., polypropylene or polyethylene), silicone, a thermoplastic elastomer, and/or a woven or non-woven fabric. A wall thickness for the housing 102 can depend on a desired stiffness or flexibility. In some examples, the wall thickness can be about 2 mm, 1 mm, 0.5 mm, or less, or can range from about 0.5 mm to about 1.5 mm (e.g., for a small injection molded part). The housing materials and/or wall thicknesses can allow the stiffness of the housing 102 to be as much as 25%, 50%, 75%, or 90% lower than the housing stiffness of existing or previous designs.

Further, in some embodiments, the pumping mechanisms described herein (e.g., including the paddle 110 and the driving bag 132) do not utilize motors, electrical components, or any electrical energy to force or pump the drug through a cannula and into a patient. The energy to pump the drug can instead be provided by springs or chemical energy, as described herein. By comparison, previous or existing devices generally include electrical or battery-powered pumps, which can be more complicated and generally less reliable or more prone to failure.

FIG. 6 is a flowchart of a method 150 of delivering a drug. A wearable drug delivery device is provided (step 152). The device includes: a housing; a flexible bag disposed within the housing; a cannula in fluid communication with the flexible bag; and a pumping mechanism having a spring-loaded paddle or a driving bag (e.g., including a plurality of reactants). The pumping mechanism is activated (step 154) to force a drug from the flexible bag and into the cannula. Activating the pumping mechanism can include, for example, compressing the flexible bag with the spring-loaded paddle or the driving bag and/or opening or closing a valve.

The teachings herein may be used to implement methods for delivering various medicaments or drugs, including but not limited to pegfilgrastim as well as other liquids, such as solutions, which may comprise any of adalimumab, rituximab, risankizumab, etanercept, trastuzumab, ado-trastuzumab emtansine, trastuzumab deruxtecan, bevacizumab, infliximab, pegfilgrastim, filgrastim, tocilizumab, golimumab, interferon beta-1a, ranibizumab, denosumab, pembrolizumab, nivolumab, aflibercept, eculizumab, ocrelizumab, pertuzumab, secukinumab, omalizumab, ustekinumab, vedolizumab, daratumumab, dupilumab, atezolizumab, natalizumab, bortezomib, ipilimumab, durvalumab, emicizumab, palivizumab, guselkumab, mepolizumab, panitumumab, ramucirumab, belimumab, abatacept, certolizumab pegol, ixekizumab, romiplostim, benralizumab, evolocumab, canakinumab, obinutuzumab, cetuximab, erenumab, blinatumomab, romosozumab, mirikizumab, inotuzumab, sacituzumab govitecan, enfortumab vedotin, brentuximab vedotin, or any combination thereof.

Each numerical value presented herein, for example, in a table, a chart, or a graph, is contemplated to represent a minimum value or a maximum value in a range for a corresponding parameter. Accordingly, when added to the claims, the numerical value provides express support for claiming the range, which may lie above or below the numerical value, in accordance with the teachings herein. Absent inclusion in the claims, each numerical value presented herein is not to be considered limiting in any regard.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention.

The features and functions of the various embodiments may be arranged in various combinations and permutations, and all are considered to be within the scope of the disclosed invention. Accordingly, the described embodiments are to be considered in all respects as only illustrative and not restrictive. Furthermore, the configurations, materials, and dimensions described herein are intended as illustrative and in no way limiting. Similarly, although physical explanations have been provided for explanatory purposes, there is no intent to be bound by any particular theory or mechanism, or to limit the claims in accordance therewith.

What is claimed is:

1. A wearable drug delivery device comprising:
   a housing;
   a flexible bag disposed within the housing;
   a cannula in fluidic communication with the flexible bag, the cannula comprising:
      a proximal end connected to the flexible bag; and
      a distal end that exits the housing;
   a support disposed between the flexible bag and at least a portion of the cannula;
   a pumping mechanism for forcing a drug from the flexible bag and into the cannula, the pumping mechanism proximate the flexible bag and comprising a spring-loaded paddle,
      wherein the spring-loaded paddle comprises a hinged connection, and
      wherein the flexible bag is compressed between the support and the spring-loaded paddle; and
   a valve positioned inside the housing and between the proximal end of the cannula and the distal end of the cannula,
      wherein the valve is configured to open and close to control a flow of the drug through the cannula.

2. The device of claim 1, wherein the spring-loaded paddle is driven by a torsion spring or a compression spring.

3. The device of claim 1, wherein the housing comprises at least one of: a flexible outer shell or a housing height less than 12 mm.

4. The device of claim 1, wherein the valve is configured to crimp or squeeze the cannula.

5. A method of delivering a drug, the method comprising:
   providing a wearable drug delivery device comprising:
      a housing;
      a flexible bag disposed within the housing;
      a cannula in fluidic communication with the flexible bag, the cannula comprising:
         a proximal end connected to the flexible bag; and
         a distal end that exits the housing;
      a support disposed between the flexible bag and at least a portion of the cannula;
      a valve positioned inside the housing and between the proximal end of the cannula and the distal end of the cannula; and
      a pumping mechanism comprising a spring-loaded paddle, wherein the spring-loaded paddle comprises a hinged connection;
   activating the pumping mechanism to force a drug from the flexible bag and into the cannula, wherein the flexible bag is compressed between the support and the spring-loaded paddle; and
   opening and closing the valve to control a flow of the drug through the cannula.

6. The method of claim 5, wherein the step of activating the pumping mechanism comprises pivoting the spring-loaded paddle about the hinged connection.

7. The method of claim 6, wherein the step of pivoting the spring-loaded paddle comprises driving the spring-loaded paddle with a torsion spring or a compression spring.

8. The method of claim 5, wherein the housing comprises at least one of: a flexible outer shell or a housing height less than 12 mm.

9. The method of claim 5, wherein the step of opening and closing the valve comprises crimping or squeezing the cannula.

10. The method of claim 5, wherein the drug comprises pegfilgrastim.

* * * * *